(12) United States Patent
Suzuki et al.

(10) Patent No.: US 7,538,250 B2
(45) Date of Patent: May 26, 2009

(54) PYRENE COMPOUND AND ORGANIC LIGHT EMITTING DEVICE

(75) Inventors: Koichi Suzuki, Yokohama (JP); Naoki Yamada, Inagi (JP); Kazunori Ueno, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/937,115

(22) Filed: Nov. 8, 2007

(65) Prior Publication Data
US 2008/0119671 A1  May 22, 2008

(30) Foreign Application Priority Data
Nov. 17, 2006  (JP) .............................. 2006-310898

(51) Int. Cl.
*C07C 211/00* (2006.01)
*C07C 13/465* (2006.01)
*C07C 2/00* (2006.01)

(52) U.S. Cl. .......................... 564/387; 564/315; 585/26; 585/500

(58) Field of Classification Search ................. 564/315, 564/387; 585/26, 500
See application file for complete search history.

(56) References Cited

U.S. PATENT DOCUMENTS

| | | | |
|---|---|---|---|
| 7,229,702 | B2 | 6/2007 | Saitoh |
| 7,241,513 | B2 | 7/2007 | Suzuki |
| 2005/0236977 | A1 | 10/2005 | Yamada |
| 2006/0113528 | A1 | 6/2006 | Okinaka |
| 2006/0115678 | A1 | 6/2006 | Saltoh |
| 2006/0121312 | A1 | 6/2006 | Yamada |
| 2007/0111029 | A1 | 5/2007 | Yamada |

FOREIGN PATENT DOCUMENTS

| | | |
|---|---|---|
| JP | 2001118682 | 4/2001 |
| JP | 2002063988 | 2/2002 |

OTHER PUBLICATIONS

Molecular Tectonics: Design of 1-D Coordination Networks Based on Pyrene-Bearing Pyrazolyl Units; vol. 2003 Issue 1, pp. 57-61, Published Online: Dec. 12, 2002.*
Miyaura, et al.; "Palladium-Catalyzed Cross Coupling Reactions of Organoboron Compounds"; pp. 2457-2483; American Chemical Society (1995).
Yamamoto, et al.; "A Novel Type of Polycondensation Utilizing Transition Metal-Catalyzed C-C Coupling. I. Preparation of Thermostable Polyphenylene Type Polymers"; Bulletin of the Chemical Society of Japan, vol. 51(7), pp. 2091-2097; (1978).

* cited by examiner

*Primary Examiner*—Jafar Parsa
(74) *Attorney, Agent, or Firm*—Fitzpatrick, Cella, Harper & Scinto

(57) ABSTRACT

An object of the present invention is to provide a novel pyrene compound. Provided is a pyrene compound represented by the following general formula (I):

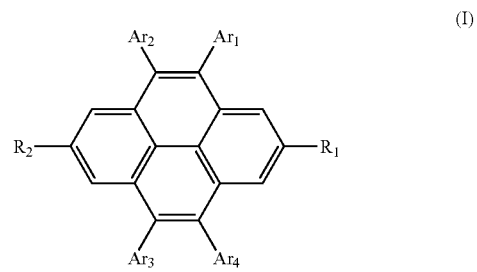

wherein: $R_1$ and $R_2$ each represent a substituted or unsubstituted alkyl group; and $Ar_1$, $Ar_2$, $Ar_3$, and $Ar_4$ each represent a substituted or unsubstituted aryl group and the like.

5 Claims, 4 Drawing Sheets

PYRENE COMPOUND AND ORGANIC LIGHT EMITTING DEVICE

BACKGROUND OF THE INVENTION

1. Field of the Invention

The present invention relates to a novel organic compound, and an organic light emitting device and an ink composition each using the compound.

2. Description of the Related Art

In order that the performance of an organic light emitting device such as light emitting efficiency, the color purity of a luminescent color, or a lifetime may be improved, a large number of materials for organic light emitting devices each having such improved performance, and a large number of organic light emitting devices each having such improved performance have been developed.

A large number of condensed polycyclic compounds have been heretofore developed to serve as singlet light emitting materials. A large number of materials for compounds each having a pyrene ring out of those condensed polycyclic compounds have been developed because the compounds each having a pyrene ring each have a relatively high fluorescent quantum efficiency. Japanese Patent Application Laid-Open No. 2001-118682 and Japanese Patent Application Laid-Open No. 2002-63988 each report an organic light emitting device using a pyrene compound having a pyrene ring as its central skeleton as a light emitting material.

At present, however, none of those organic light emitting devices each using a pyrene compound has sufficient initial characteristics such as light emitting efficiency, and a sufficient duration characteristic against, for example, luminance degradation due to long-term light emission.

SUMMARY OF THE INVENTION

In view of the foregoing, an object of the present invention is to provide a novel pyrene compound.

Another object of the present invention is to provide an organic light emitting device using the novel pyrene compound, and having high light emitting efficiency and high durability.

Another object of the present invention is to provide an organic light emitting device that can be easily produced by a coating method that is relatively low cost.

Another object of the present invention is to provide an ink composition using the novel pyrene compound.

Another object of the present invention is to provide a display panel or display apparatus including the above organic light emitting device.

The inventors of the present invention have found that an organic light emitting device using a layer containing a specific pyrene compound, in particular, a light emitting layer containing the compound has excellent initial characteristics and an excellent duration characteristic. Thus, the inventors have completed the present invention.

That is, the present invention provides a pyrene compound represented by the following general formula (I):

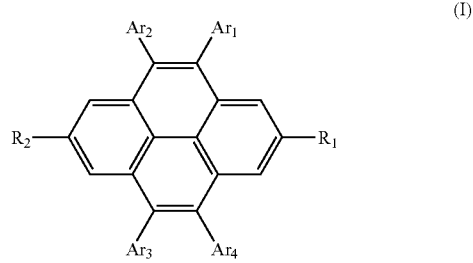

(I)

In the general formula (I), $R_1$ and $R_2$ each represent a substituted or unsubstituted alkyl group, and $R_1$ and $R_2$ may be identical to or different from each other.

$Ar_1$, $Ar_2$, $Ar_3$, and $Ar_4$ each represent a group selected from the group consisting of a substituted or unsubstituted aryl group, a substituted or unsubstituted heterocyclic group, a substituted or unsubstituted condensed polycyclic aromatic group, and a substituted or unsubstituted condensed polycyclic heterocyclic group, and $Ar_1$, $Ar_2$, $Ar_3$, and $Ar_4$ may be identical to or different from each other.

According to the present invention, there can be provided a novel pyrene compound.

In addition, an organic light emitting device and display apparatus having high light emitting efficiency and high durability can be provided by using the pyrene compound of the present invention.

In addition, an organic light emitting device and display apparatus which can be easily produced by a coating method that is relatively low cost can be provided by using an ink composition containing the pyrene compound of the present invention.

Further features of the present invention will become apparent from the following description of exemplary embodiments with reference to the attached drawings.

DESCRIPTION OF THE EMBODIMENTS

Figure 1:
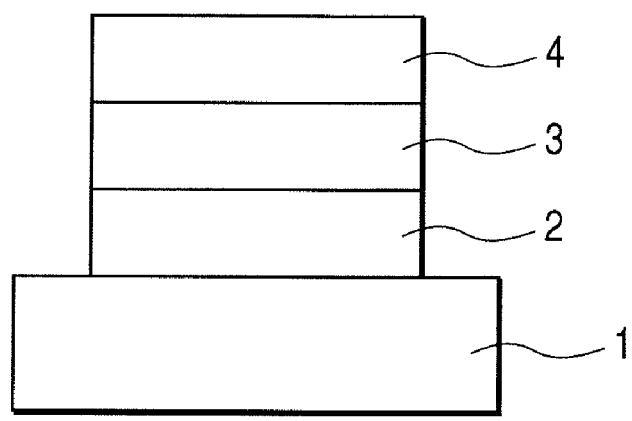
FIG. 1 is a sectional view illustrating an example of an organic light emitting device in the present invention.

Hereinafter, the present invention will be described in detail.

First, a pyrene compound of the present invention will be described. The pyrene compound of the present invention is represented by the above general formula (I).

Preferable examples of the pyrene compound of the present invention include compounds in each of which $Ar_1$, $Ar_2$, $Ar_3$, and $Ar_4$ in the general formula (I) are each represented by any one of the following general formulae (II) to (VI):

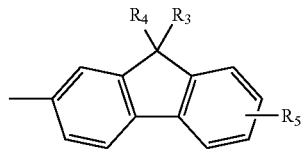

(II)

In the general formula (II), $R_3$ and $R_4$ each represent a group selected from the group consisting of a substituted or unsubstituted alkyl group, a substituted or unsubstituted aralkyl group, a substituted or unsubstituted aryl group, and a substituted or unsubstituted heterocyclic group, and $R_3$ and $R_4$ may be identical to or different from each other.

$R_5$ represents a group selected from the group consisting of a hydrogen atom, a substituted or unsubstituted alkyl group, a substituted or unsubstituted aralkyl group, a substituted or unsubstituted aryl group, a substituted or unsubstituted heterocyclic group, a substituted or unsubstituted condensed polycyclic aromatic group, a substituted or unsubstituted condensed polycyclic heterocyclic group, a substituted or unsubstituted aryloxy group, a substituted amino group, a halogen atom, and a cyano group.

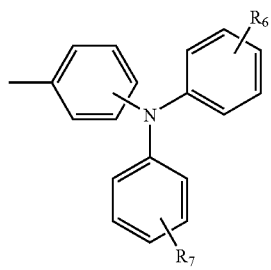

(III)

In the general formula (III), $R_6$ and $R_7$ each represent a group selected from the group consisting of a hydrogen atom, a substituted or unsubstituted alkyl group, a substituted or unsubstituted aralkyl group, a substituted or unsubstituted aryl group, a substituted or unsubstituted heterocyclic group, a substituted or unsubstituted condensed polycyclic aromatic group, a substituted or unsubstituted condensed polycyclic heterocyclic group, a substituted or unsubstituted aryloxy group, a substituted amino group, a halogen atom, and a cyano group, and $R_6$ and $R_7$ may be identical to or different from each other.

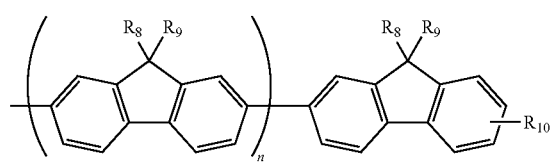

(IV)

In the general formula (IV), $R_8$ and $R_9$ each represent a group selected from the group consisting of an alkyl group, a substituted or unsubstituted aralkyl group, a substituted or unsubstituted aryl group, and a substituted or unsubstituted heterocyclic group, and $R_8$ and $R_9$ may be identical to or different from each other.

$R_{10}$ represents a group selected from the group consisting of a hydrogen atom, a substituted or unsubstituted alkyl group, a substituted or unsubstituted aralkyl group, a substituted or unsubstituted aryl group, a substituted or unsubstituted heterocyclic group, a substituted or unsubstituted condensed polycyclic aromatic group, a substituted or unsubstituted condensed polycyclic heterocyclic group, a substituted or unsubstituted aryloxy group, a substituted amino group, a halogen atom, and a cyano group.

n represents an integer of 1 or more to 9 or less.

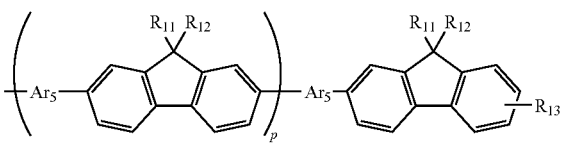

(V)

In the general formula (V), $R_{11}$ and $R_{12}$ each represent a group selected from the group consisting of an alkyl group, a substituted or unsubstituted aralkyl group, a substituted or unsubstituted aryl group, and a substituted or unsubstituted heterocyclic group, and $R_{11}$ and $R_{12}$ may be identical to or different from each other.

$R_{13}$ represents a group selected from the group consisting of a hydrogen atom, a substituted or unsubstituted alkyl group, a substituted or unsubstituted aralkyl group, a substituted or unsubstituted aryl group, a substituted or unsubstituted heterocyclic group, a substituted or unsubstituted condensed polycyclic aromatic group, a substituted or unsubstituted condensed polycyclic heterocyclic group, a substituted or unsubstituted aryloxy group, a substituted amino group, a halogen atom, and a cyano group.

$Ar_5$ represents a divalent, substituted or unsubstituted aryl group, or a divalent, substituted or unsubstituted condensed polycyclic aromatic group.

p represents an integer of 0 or more to 5 or less.

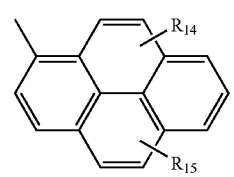

(VI)

In the general formula (VI), $R_{14}$ and $R_{15}$ each represent a group selected from the group consisting of a hydrogen atom, a substituted or unsubstituted alkyl group, a substituted or unsubstituted aralkyl group, a substituted or unsubstituted aryl group, a substituted or unsubstituted heterocyclic group, a substituted or unsubstituted condensed polycyclic aromatic group, a substituted or unsubstituted condensed polycyclic heterocyclic group, a substituted or unsubstituted aryloxy group, a substituted amino group, a halogen atom, and a cyano group, and $R_{14}$ and $R_{15}$ may be identical to or different from each other.

Specific examples of substituents in the general formulae (I) to (VI) are shown below.

Alkyl groups include a methyl group, an ethyl group, an n-propyl group, an n-butyl group, a t-butyl group, a 3-methylbutyl group, a 2-ethylhexyl group, and an octyl group.

Aralkyl groups include a benzyl group and a phenethyl group.

Aryl groups include a phenyl group, a biphenyl group, an m-terphenyl group, and a p-terphenyl group.

Heterocyclic groups include a thienyl group, a pyrolyl group, a pyridyl group, a bipyridyl group, an oxazolyl group, an oxadiazolyl group, a thiazolyl group, and a thiadiazolyl group.

Examples of the condensed polycyclic aromatic group include a fluorenyl group, a naphthyl group, an anthracenyl group, a phenanthrenyl group, a fluorantenyl group, a pyrenyl group, and a perylenyl group.

Examples of the condensed polyheterocyclic group include a quinolyl group, a carbazolyl group, an acrydinyl group, and a phenanthrolyl group.

Examples of the aryloxy group include a phenoxyl group and a naphthoxyl group.

Examples of the substituted amino group are as follows: a dimethylamino group; a diethylamino group; a diphenylamino group; a ditolylamino group; a di-t-butylphenylamino group; a dianisolylamino group; a fluorenylphenylamino group; a difluorenylamino group; a naphthylphenylamino group; and a dinaphthylamino group.

Examples of the halogen atom include fluorine, chlorine, bromine, and iodine.

Examples of the divalent aryl group include a phenylene group, a biphenylene group, an m-terphenylene group, and a p-terphenylene group.

Examples of the divalent condensed polycyclic heterocyclic group include a fluorenylene group, a naphthylene group, an anthracenylene group, and a fluorantenylene group.

Examples of the substitutent the above-mentioned substitutents can contain are as follows: alkyl groups such as a methyl group, an ethyl group, an n-propyl group, an n-butyl group, a t-butyl group, a 3-methylbutyl group, a 2-ethylhexyl group, and an octyl group; aralkyl groups such as a benzyl group and a phenetyl group; aryl groups such as a phenyl group, a biphenyl group, an m-terphenyl group, and a p-terphenyl group; heterocyclic groups such as a thienyl group, a pyrrolyl group, a pyridyl group, a bipyridyl group, an oxazolyl group, an oxadiazolyl group, a thiazolyl group, and a thiadiazolyl group; condensed polycyclic aromatic groups such as a fluorenyl group, a naphthyl group, an anthranyl group, a phenanthryl group, a fluorantenyl group, and a pyrenyl group; condensed polycyclic heterocyclic groups such as a quinolyl group, a carbazolyl group, an acrydinyl group, and a phenanthrolyl group; aryloxy groups such as a phenoxyl group and a naphthoxyl group; substituted amino groups such as a dimethylamino group, a diethylamino group, a diphenylamino group, a ditolylamino group, a di-t-butylphenylamino group, a dianisolylamino group, a fluorenylphenylamino group, a difluorenylamino group, a naphthylphenylamino group, and a dinaphthylamino group; and halogen atoms such as fluorine, chlorine, bromine, and iodine.

Next, representative examples of the pyrene compound of the present invention are shown below. However, the compound of the present invention is not limited to these examples. It should be noted that only a substituent is shown except for Compound No. 1; in any compound, $Ar_1$, $Ar_2$, $Ar_3$, and $Ar_4$ each have any one of the following substituents as in the case of Compound No. 1.

COMPOUND EXAMPLE NO. 1

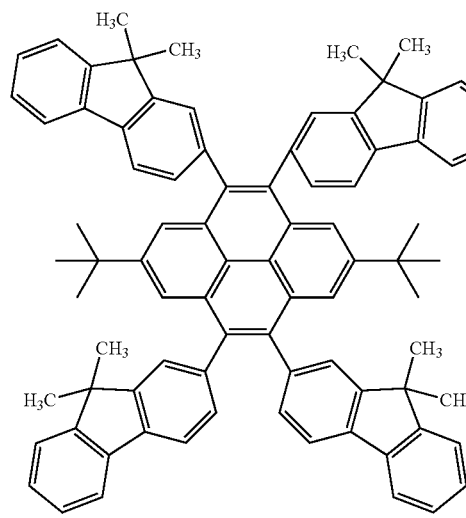

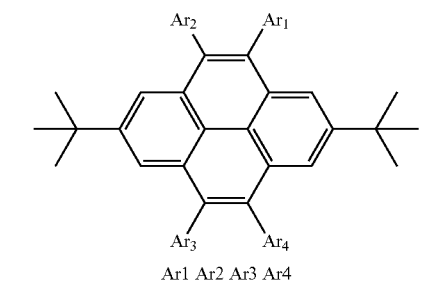

Ar1 Ar2 Ar3 Ar4

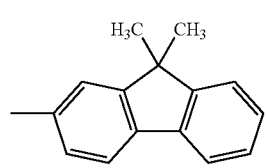

1

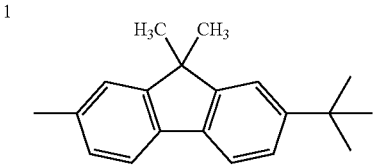

2

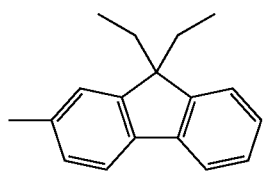
3
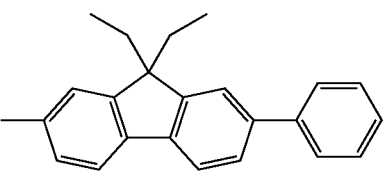
4
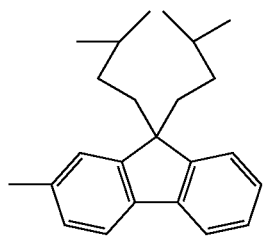
5
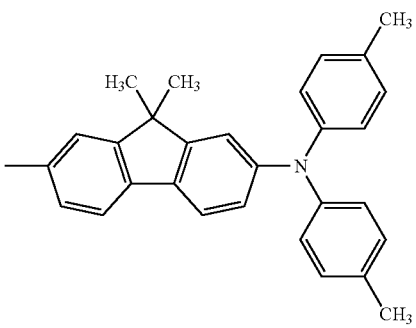
6
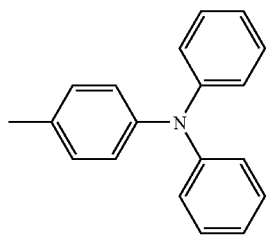
7
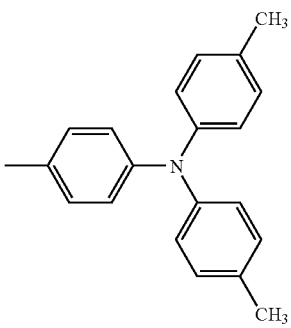
8
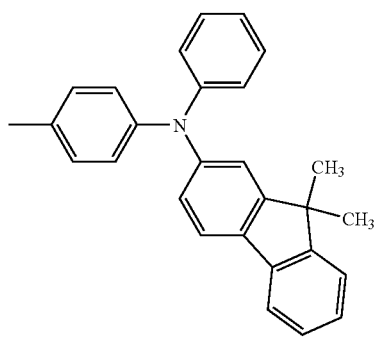
9
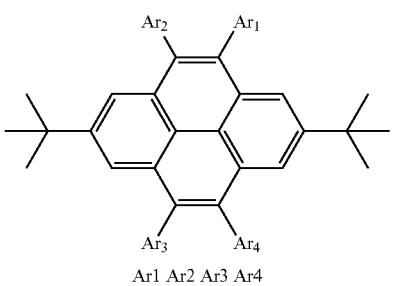
Ar1 Ar2 Ar3 Ar4
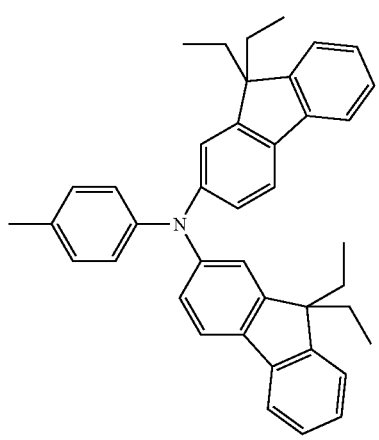
10

-continued
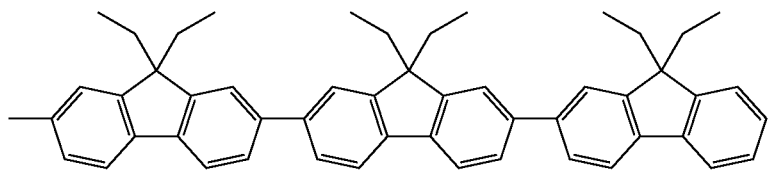
11
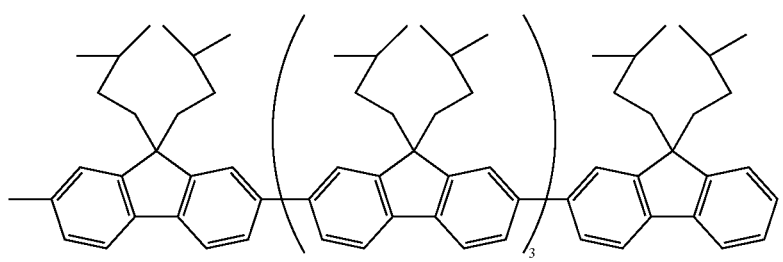
12
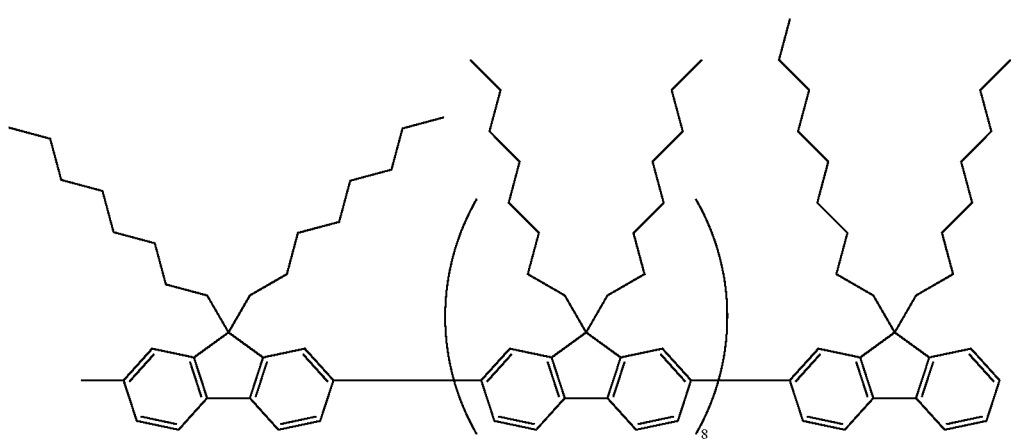
13
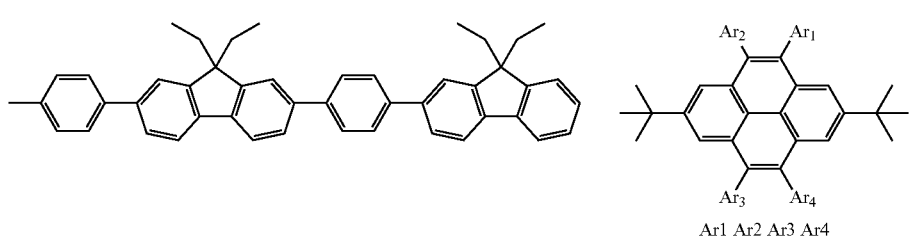
14
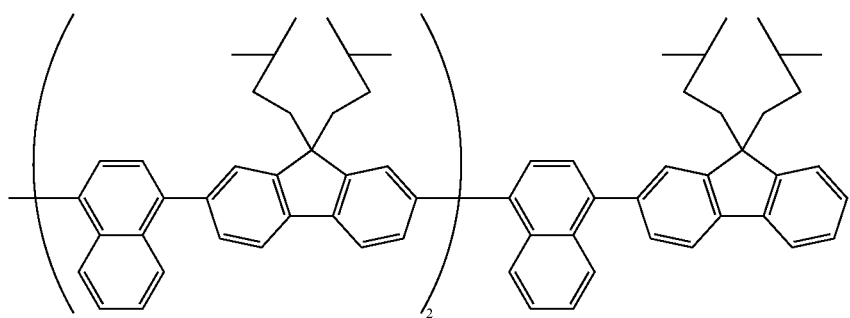
15
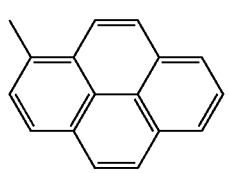
16
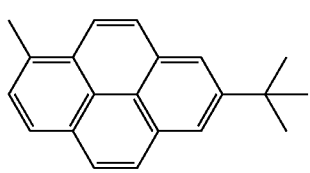
17

-continued
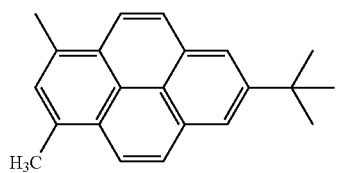
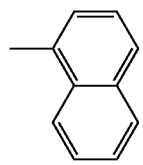
18
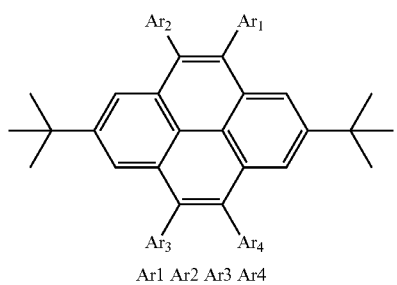
Ar1 Ar2 Ar3 Ar4
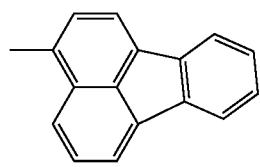
20
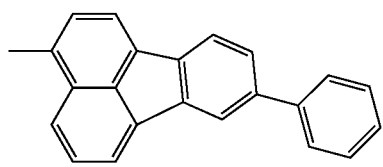
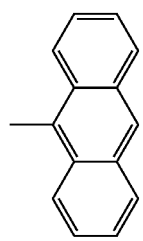
21
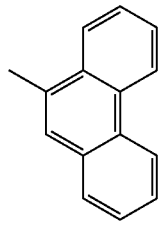
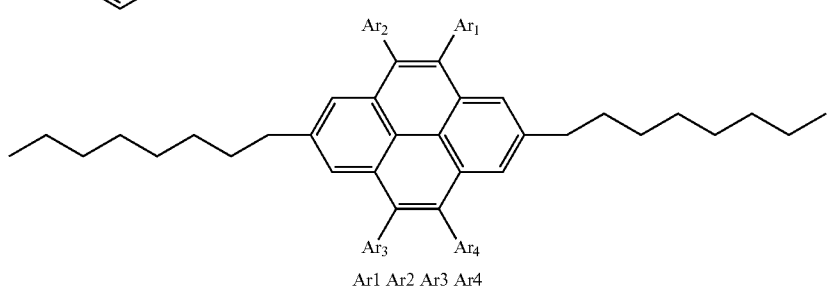
Ar1 Ar2 Ar3 Ar4
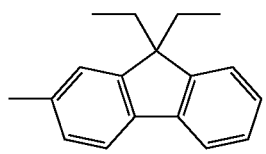
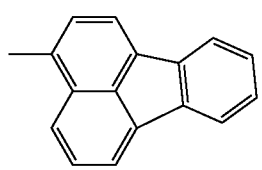
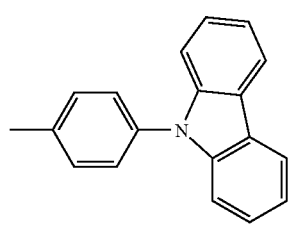
19
22
23
24
25
26
27

The pyrene compound of the present invention can be synthesized by a generally known method, and can be obtained by, for example, each of the following synthesis methods: a Suzuki Coupling method using a palladium catalyst (for example, Chem. Rev., 95, 2457, 1995) and a Yamamoto method using a nickel catalyst (for example, Bull. Chem. Soc. Jpn. 51, 2091, 1978).

The pyrene compound of the present invention is superior to a conventional compound in light emitting property and durability, and is useful in a layer containing an organic compound of an organic light emitting device, in particular, a light emitting layer of the device. In addition, a layer formed of the compound by a vacuum deposition method or a solution coating method hardly undergoes crystallization or the like, and is excellent in stability over time.

Next, an organic light emitting device of the present invention will be described in detail.

The organic light emitting device of the present invention includes: a pair of electrodes formed of an anode and a cathode; and one or more layers each containing an organic compound, the one or more layers being interposed between the pair of electrodes. In addition, at least one layer of the one or more layers each containing an organic compound, preferably a light emitting layer, contains at least one kind of the above pyrene compound of the present invention.

When the pyrene compound of the present invention is used as a guest material for the light emitting layer, the content of the compound is preferably 0.1 wt % or more to 50 wt % or less, or more preferably 0.5 wt % or more to 30 wt % or less.

In addition, when the pyrene compound of the present invention is used as a host material for the light emitting layer, the content of the compound is preferably 50 wt % or more to 99.9 wt % or less, or more preferably 70 wt % or more to 99.5 wt % or less.

A layer containing the pyrene compound of the present invention is formed by a vacuum deposition method or a solution coating method between the anode and the cathode. When the pyrene compound of the present invention has a molecular weight of 1,200 or more, the solution coating method is preferably adopted because the compound tends to have a high sublimation temperature. The layer containing the pyrene compound of the present invention has a thickness of less than 10 µm, and is formed into a thin film having a thickness of preferably 0.5 µm or less, or more preferably 0.01 µm or more to 0.5 µm or less.

The organic light emitting device of the present invention may have plural organic layers in addition to the light emitting layer, and examples of the layers include a hole injecting layer, a hole transporting layer, a hole/exciton blocking layer, an electron transporting layer, and an electron injecting layer. Each of those layers is produced by a vacuum deposition method or a solution coating method, and has a thickness of less than 5 µm, preferably 1 µm or less, or more preferably 10 nm or more to 500 nm or less.

FIGS. 1 to 7 each show a preferable example of the organic light emitting device of the present invention.

FIG. 1 is a sectional view illustrating an example of the organic light emitting device of the present invention. FIG. 1 illustrates a constitution in which an anode 2, a light emitting layer 3, and a cathode 4 are sequentially provided on a substrate 1. The light emitting device to be used here is useful when a single compound having a hole transporting ability, an electron transporting ability, and light emitting property by itself is used, or when compounds having the respective properties are used as a mixture.

Figure 2:
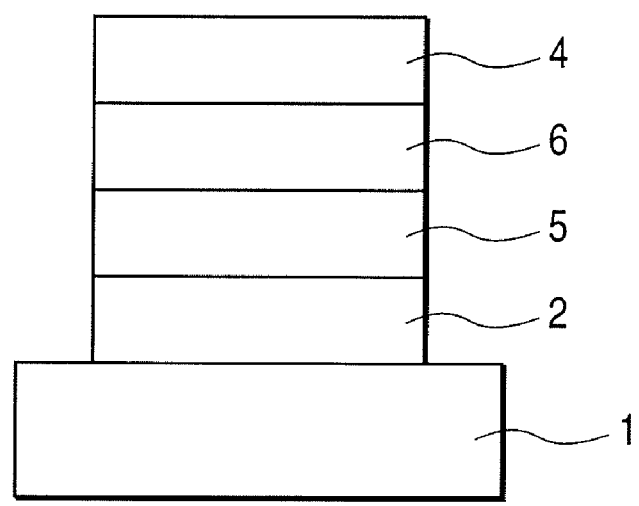
FIG. 2 is a sectional view illustrating another example of the organic light emitting device in the present invention.

FIG. 2 is a sectional view illustrating another example of the organic light emitting device of the present invention. FIG. 2 illustrates a constitution in which the anode 2, a hole transporting layer 5, an electron transporting layer 6, and the cathode 4 are sequentially provided on the substrate 1. The case is useful when a material having one or both of hole transporting property and electron transporting property is used as a light emitting substance, and is used in combination with a mere hole transporting substance or electron transporting substance which does not have a light emitting property. In addition, in this case, the light emitting layer is formed of one of the hole transporting layer 5 and the electron transporting layer 6.

Figure 3:
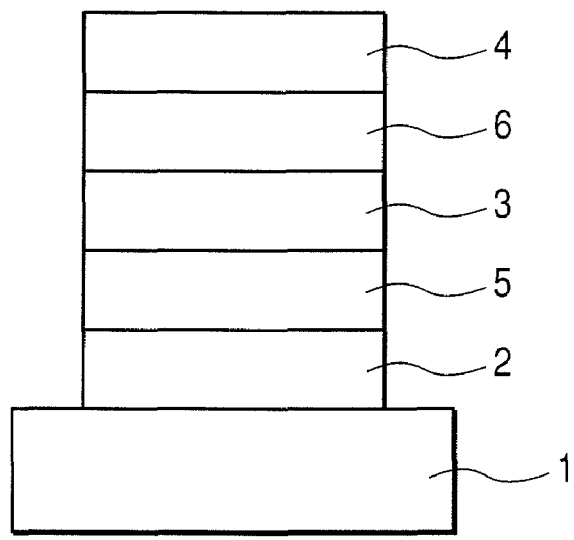
FIG. 3 is a sectional view illustrating another example of the organic light emitting device in the present invention.

FIG. 3 is a sectional view illustrating another example of the organic light emitting device of the present invention. FIG. 3 illustrates a constitution in which the anode 2, the hole transporting layer 5, the light emitting layer 3, the electron transporting layer 6, and the cathode 4 are sequentially provided on the substrate 1. In the constitution, a carrier transporting function and a light emitting function are separated from each other, and compounds having the respective properties, that is, hole transporting property, electron transporting property, and light emitting property are appropriately used in combination. As a result, a degree of freedom in the selection of materials extremely increases, and various compounds having different emission wavelengths can be used, thereby allowing an increase in variety of luminescent colors. Further, the light emitting efficiency of the device can be improved by effectively trapping each carrier or exciton in the light emitting layer 3 provided in the middle of the device.

Figure 4:
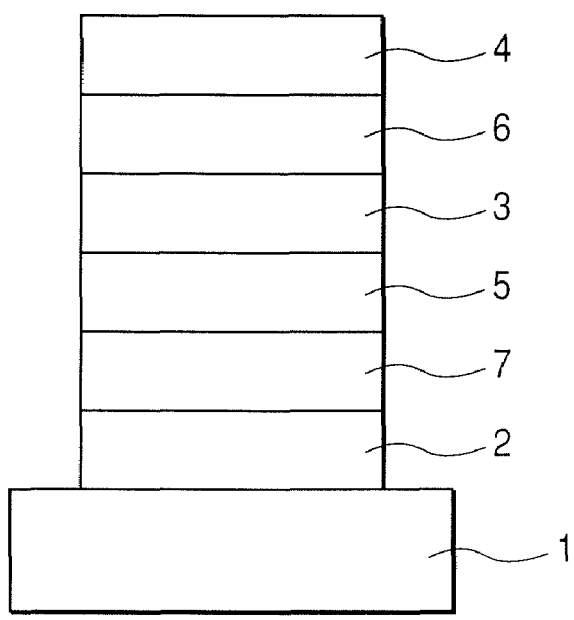
FIG. 4 is a sectional view illustrating another example of the organic light emitting device in the present invention.

FIG. 4 is a sectional view illustrating another example of the organic light emitting device of the present invention. FIG. 4 illustrates a constitution different from that shown in FIG. 3 in that a hole injecting layer 7 is inserted on the side of the anode 2. The layer has an improving effect on adhesiveness between the anode 2 and the hole transporting layer 5 or on hole injecting property, and is effective for a reduction in voltage at which the device is driven.

Figure 5:
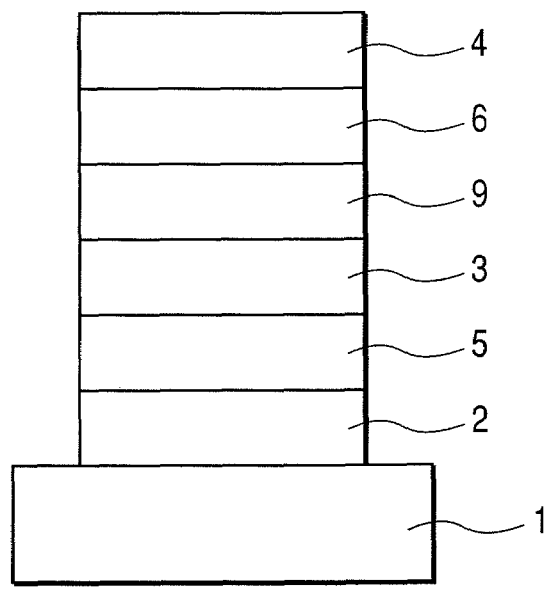
FIG. 5 is a sectional view illustrating another example of the organic light emitting device in the present invention.

FIG. 5 is a sectional view illustrating another example of the organic light emitting device of the present invention. FIG. 5 illustrates a constitution different from that shown in FIG. 3 in that a hole/exciton blocking layer 9 is inserted between the light emitting layer 3 and the electron transporting layer 6. The constitution is effective for an improvement in light emitting efficiency of the device because the escape of a hole or an exciton from the light emitting layer 3 toward the cathode 4 is suppressed by the layer 9.

Figure 6:
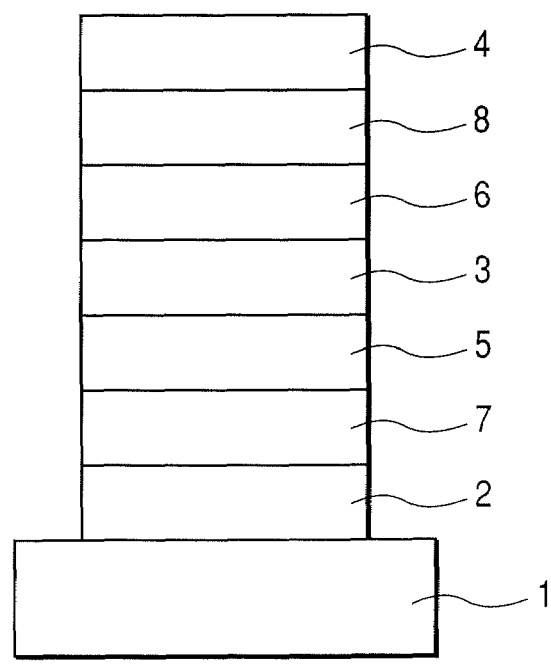
FIG. 6 is a sectional view illustrating another example of the organic light emitting device in the present invention.

FIG. 6 is a sectional view illustrating another example of the organic light emitting device of the present invention. FIG. 6 illustrates a constitution different from that shown in FIG. 4 in that an electron injecting layer 8 is inserted between the electron transporting layer 6 and the cathode 4. The constitution is effective for a reduction in voltage at which the device is driven.

Figure 7:
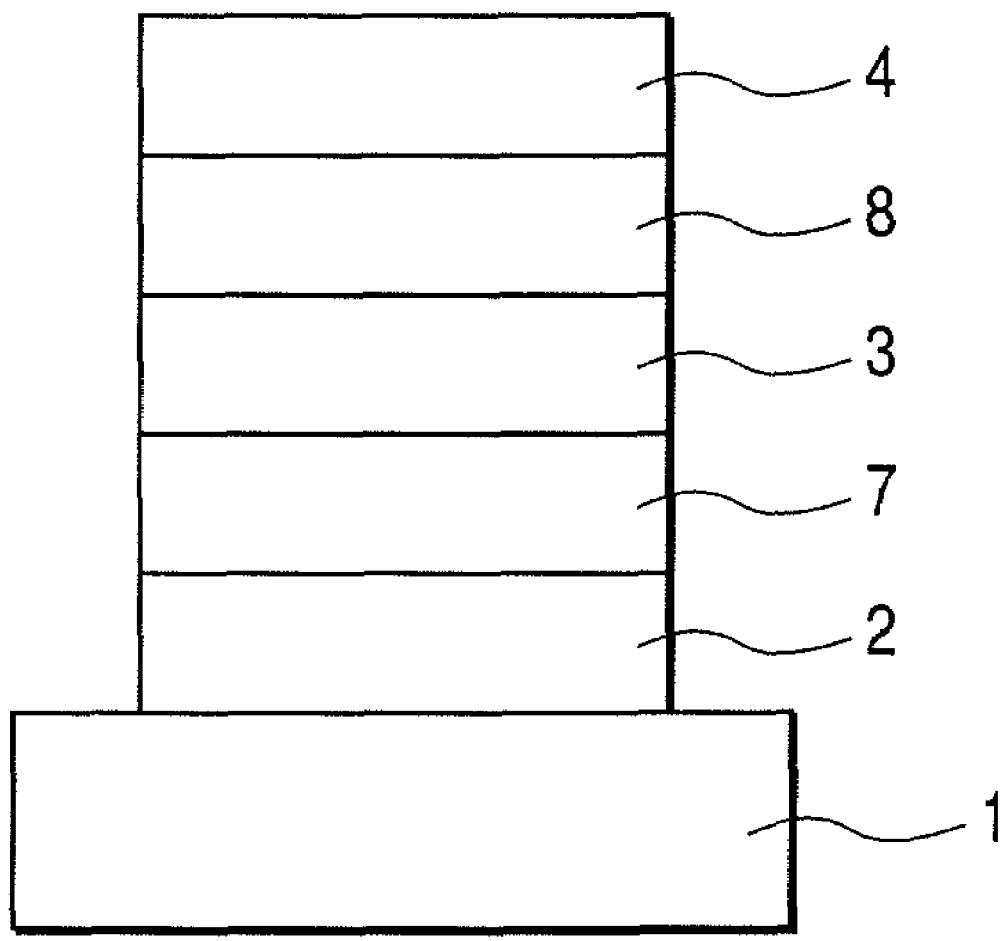
FIG. 7 is a sectional view illustrating another example of the organic light emitting device in the present invention.

FIG. 7 is a sectional view illustrating another example of the organic light emitting device of the present invention. FIG. 7 illustrates a constitution in which the anode 2, the hole injecting layer 7, the light emitting layer 3, the electron injecting layer 8, and the cathode 4 are sequentially provided on the substrate 1.

It should be noted that FIGS. 1 to 7 each merely illustrate an extremely basic device constitution, and the constitution of the organic light emitting device of the present invention is not limited to those shown in the figures. The device can adopt any one of various layer constitutions such as: a constitution in which an insulating layer is provided at an interface between an electrode and an organic layer; a constitution in which an adhesive layer or an interference layer is provided; and a constitution in which a hole injecting layer or a hole transporting layer is formed of two layers with different ionization potentials.

In the organic light emitting device of the present invention, the pyrene compound can be used in combination with, for example, a known hole transportable compound, luminescent compound, or electron transportable compounds.

Examples of those known compounds are shown below.

Hole transportable compounds

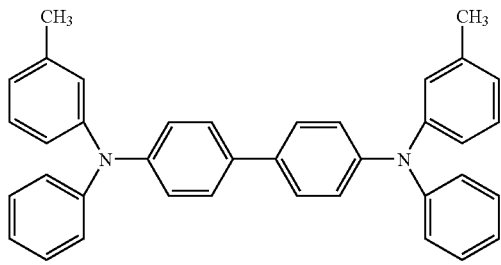

TPD

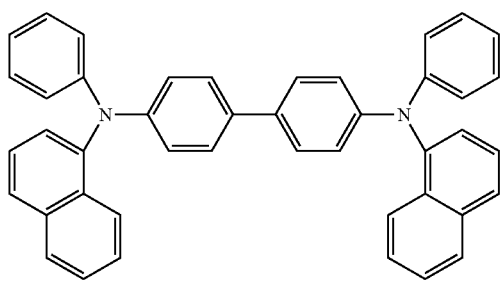

α-NPD

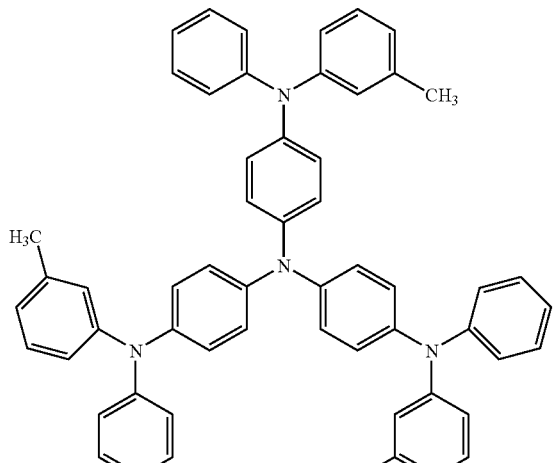

m-MTDATA

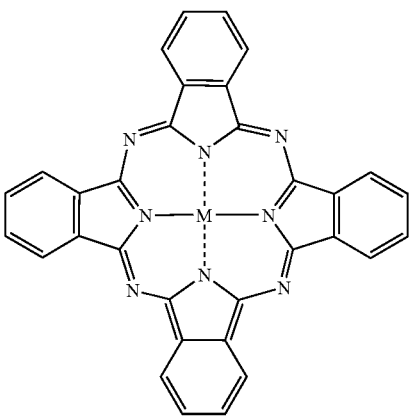

Met: Cu, Mg, AlCl, TiO, SiCl$_2$, etc
Met-Pc

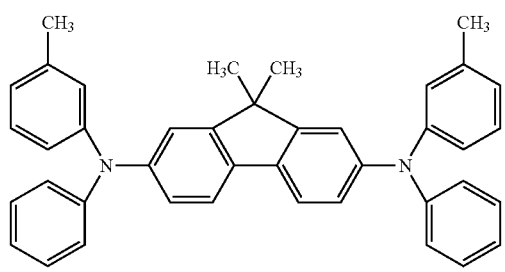

DTDPFL

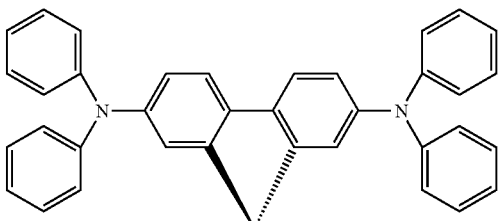

spiro-TPD

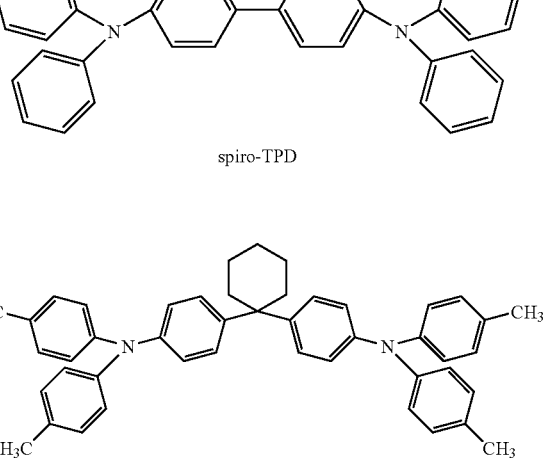

TPAC

-continued
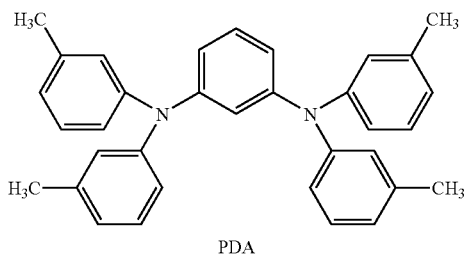
PDA
Luminescent compounds and electron transportable compounds
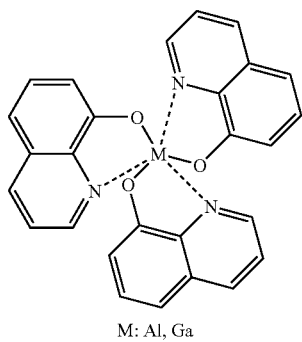
M: Al, Ga
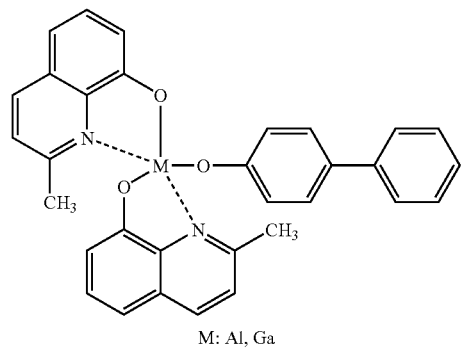
M: Al, Ga
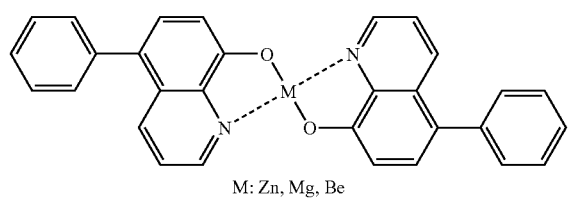
M: Zn, Mg, Be
M: Zn, Mg, Be
-continued
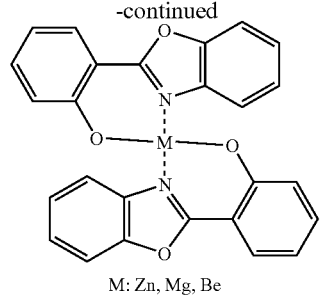
M: Zn, Mg, Be
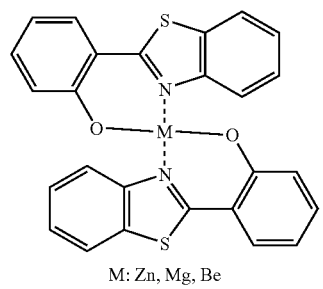
M: Zn, Mg, Be
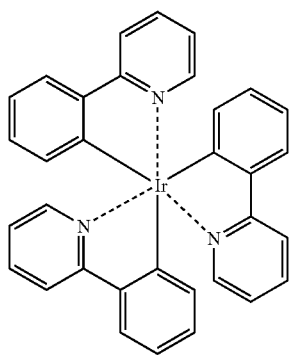
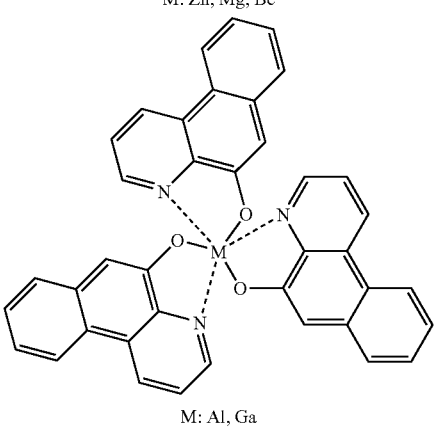
M: Zn, Mg, Be
M: Al, Ga Luminescent compounds
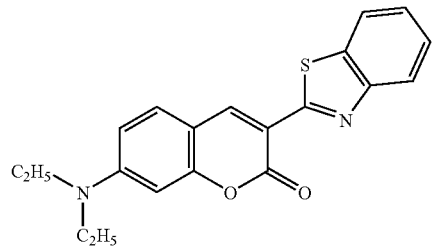
Coumarin6
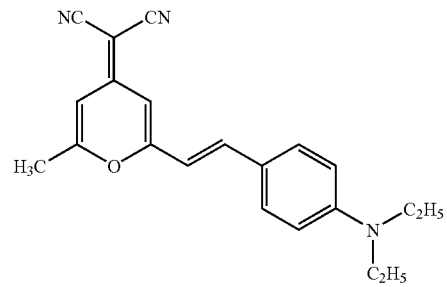
DCM-1
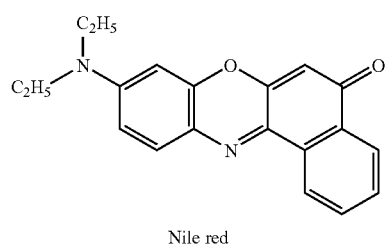
Nile red
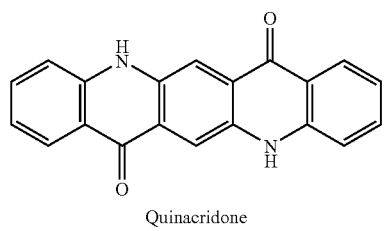
Quinacridone
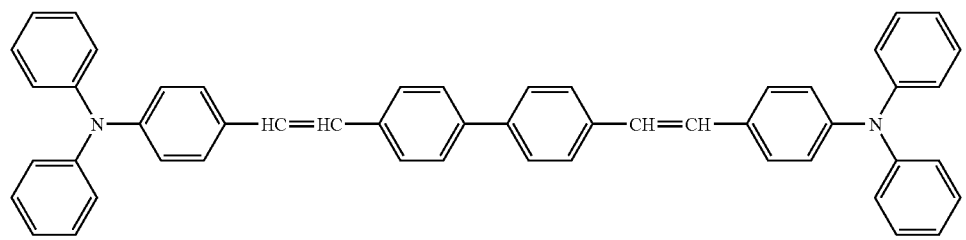
DTPABVi
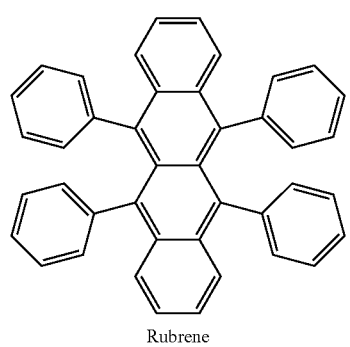
Rubrene
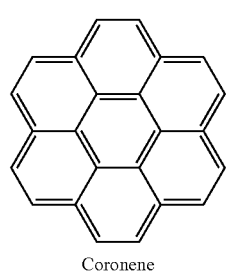
Coronene
Electron transportable compounds
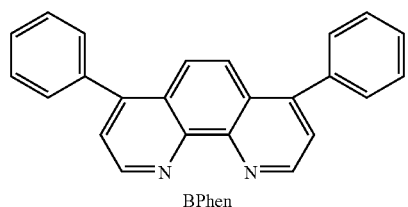
BPhen
-continued
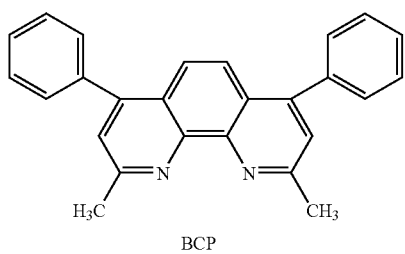
BCP -continued
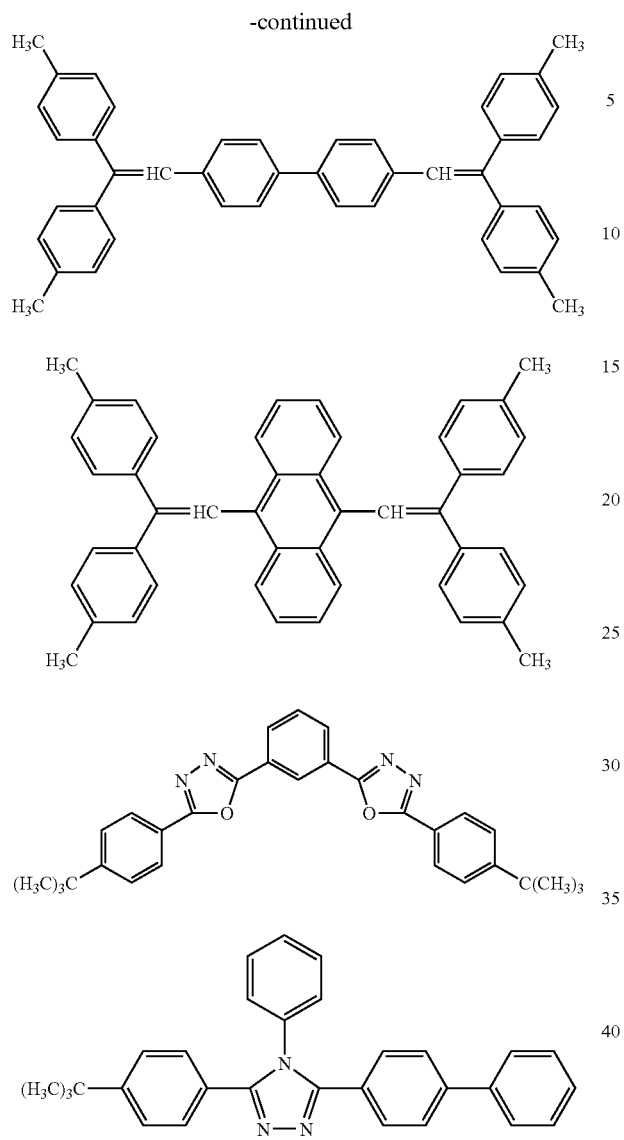
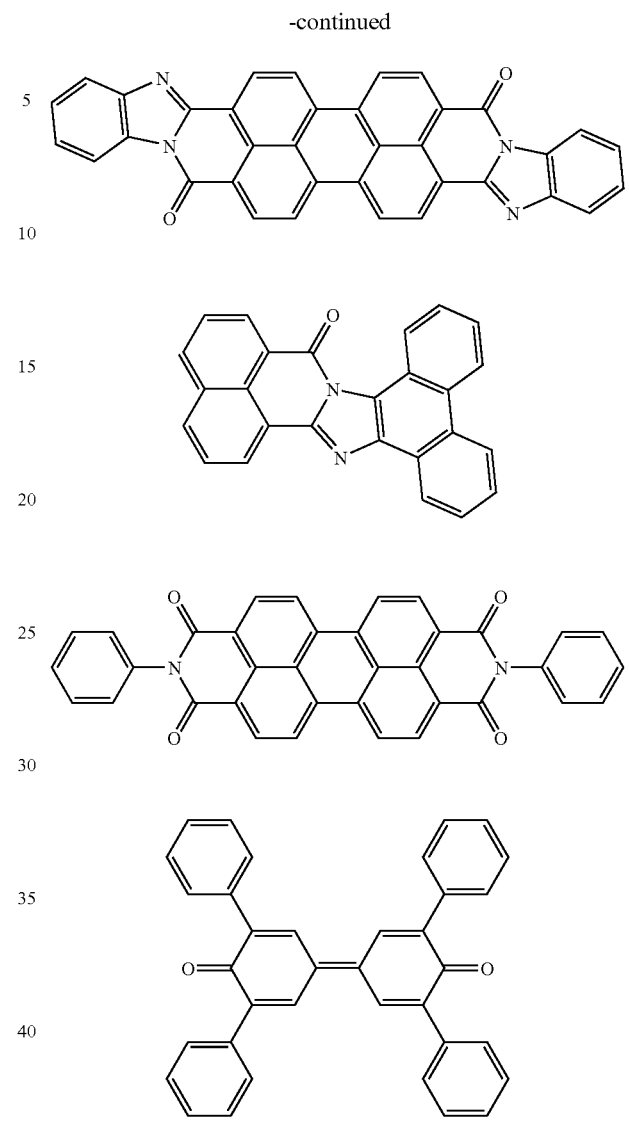
Polymer-based hole transportable compounds
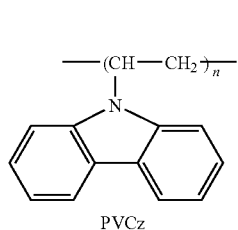
PVCz
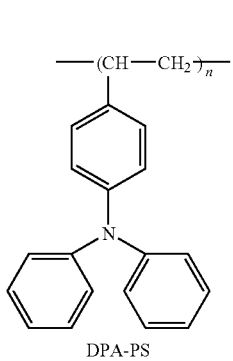
DPA-PS
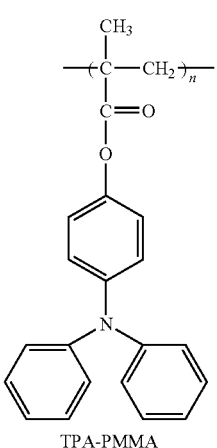
TPA-PMMA -continued
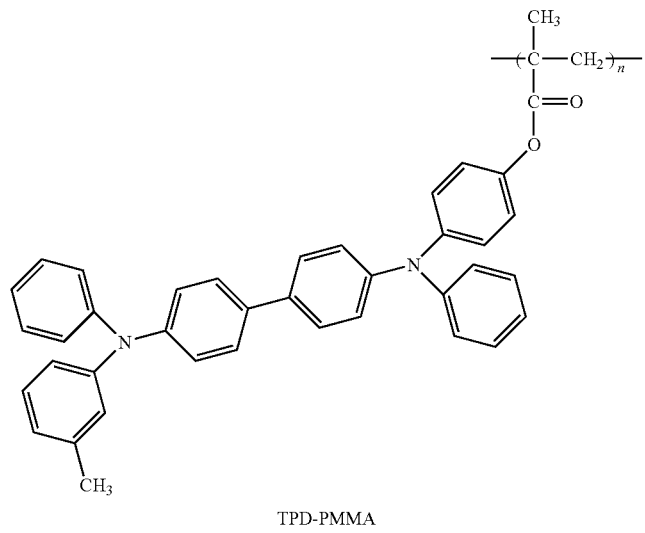
TPD-PMMA
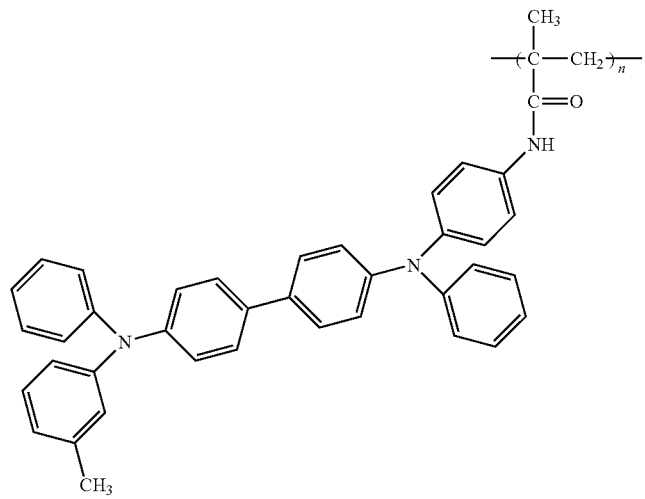
TPD-PMAA
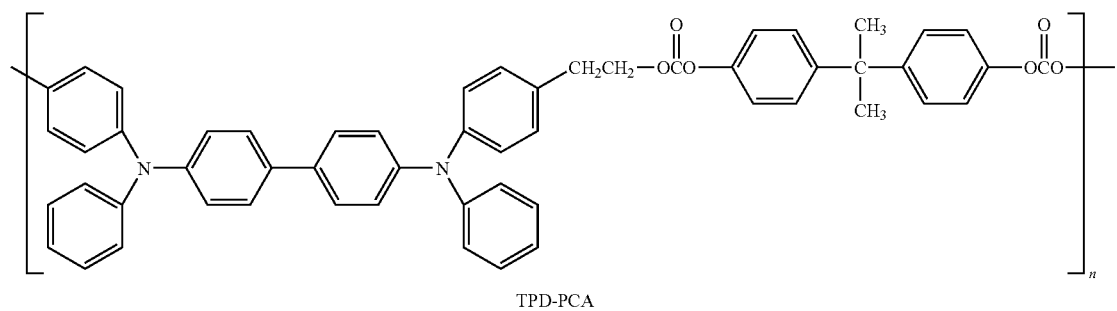
TPD-PCA

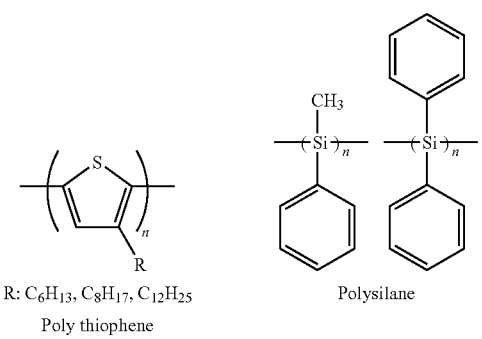

R: C$_6$H$_{13}$, C$_8$H$_{17}$, C$_{12}$H$_{25}$
Poly thiophene

Polysilane

Polymer-based luminescent compounds

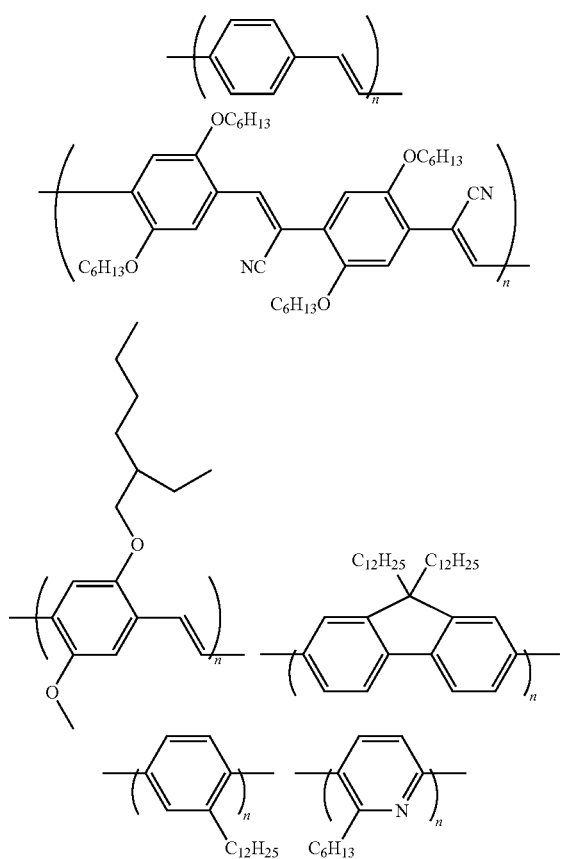

The layer containing the pyrene compound of the present invention and any other layer containing an organic compound in the organic light emitting device of the present invention are each generally formed into a thin film by a vacuum deposition method or an application method involving the use of a solution prepared by dissolving a material for any such layer in a proper solvent. Examples of the application method include a spin coating method, a slit coater method, a printing method, an ink-jet method, a dispense method, and a spray method.

In particular, when each of the layers is formed by the coating method, the layer can be formed by using a material for the layer in combination with a proper binder resin.

The above binder resin can be selected from a wide variety of binding resins, and examples of the binder resin include, but not limited to, the following resins. In addition, one kind of those resins may be used alone, or two or more kinds of them may be mixed to serve as a copolymer.

A polyvinyl carbazole resin, a polycarbonate resin, a polyester resin, a polyallylate resin, a polystyrene resin, an acrylic resin, a methacrylic resin, a butyral resin, a polyvinyl acetal resin, a diallyl phthalate resin, a phenol resin, an epoxy resin, a silicone resin, a polysulfone resin, and a urea resin.

An anode material may have as large a work function as possible, and examples thereof include: a metal element such as gold, silver, platinum, nickel, palladium, cobalt, selenium, or vanadium, or alloys thereof; and a metal oxide such as tin oxide, zinc oxide, indium tin oxide (ITO), or indium zinc oxide. Further, conductive polymers such as polyaniline, polypyrrole, polythiophene, or polyphenylene sulfide may also be used. Each of those electrode materials may be used alone, or two or more kinds thereof may be used in combination.

Meanwhile, a cathode material has preferably a small work function, and examples thereof include: a metal element such as lithium, sodium, potassium, cesium, calcium, magnesium, aluminum, indium, silver, lead, tin, chromium, alloys thereof, or salts thereof. A metal oxide such as indium tin oxide (ITO) may also be used. Further, the cathode may have a single layer structure or a multilayer structure.

The substrate to be used in the present invention is not particularly limited. Examples thereof include: opaque substrates such as a metallic substrate and a ceramics substrate; and transparent substrates such as a glass substrate, a quartz substrate, and a plastic sheet substrate. In addition, the substrate may have a color filter film, a fluorescent color converting filter film, a dielectric reflection film, or the like for controlling luminescent color.

Further, a protective layer or a sealing layer may be formed on the produced device to prevent contact between the device and oxygen, moisture, or the like. Examples of the protective layer include: a diamond thin film; a film formed of an inorganic material such as metal oxide or metal nitride; a polymer film formed of a fluorine resin, polyparaxylene, polyethylene, a silicone resin, a polystyrene resin, or the like; and a photocurable resin. Further, the device itself may be covered with glass, an airtight film, a metal, or the like and packaged with an appropriate sealing resin.

A display apparatus such as a display can be obtained by using the organic light emitting device of the present invention.

Next, an ink composition of the present invention will be described.

The ink composition of the present invention contains at least one kind of the pyrene compound of the present invention. The use of the ink composition of the present invention allows an organic compound layer of an organic light emitting device, in particular, a light emitting layer of the device to be produced by an application method, and allows a large-area device to be easily produced at a relatively low cost. In particular, when the pyrene compound has a molecular weight of 1,200 or more, the compound is suitably dissolved in a solvent so as to be used in the form of an ink composition because the compound tends to have a high sublimation temperature.

Examples of the solvent include toluene, xylene, mesitylene, dioxane, tetralin, n-dodecylbenzene, methylnaphthalene, tetrahydrofuran, diglyme, and 1,2-dichlorobenzene.

In addition, a compound the ink composition may contain in addition to the pyrene compound of the present invention is, for example, the above-mentioned known hole transportable compound, luminescent compound, or electron transportable compound.

The content of the pyrene compound of the present invention in the ink composition is preferably 0.05 wt % or more to 20 wt % or less, or more preferably 0.1 wt % or more to 5 wt % or less.

Hereinafter, the present invention will be described more specifically by way of examples. However, the present invention is not limited to these examples.

(Synthesis of Intermediate)

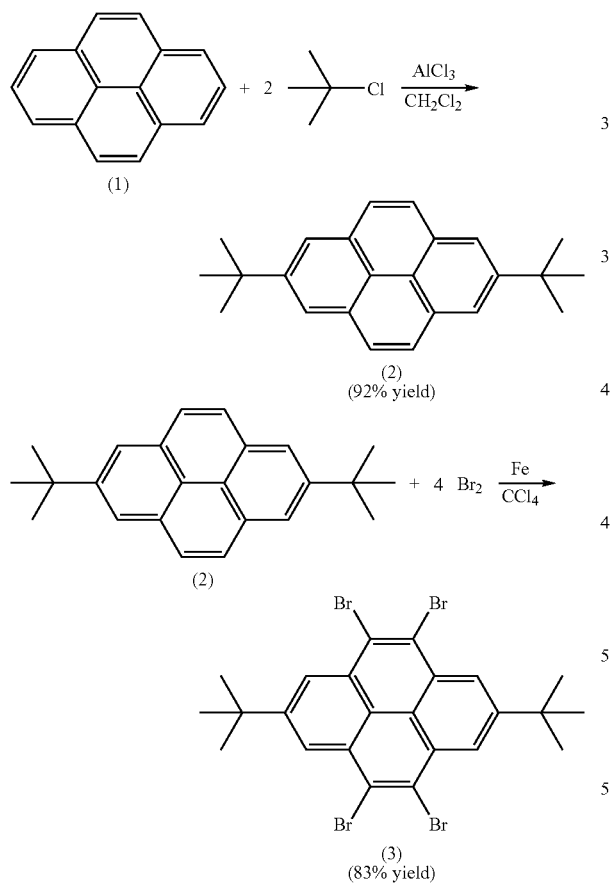

20 g (98.9 mmol) of pyrene (1) and 200 ml of dichloromethane were loaded into a 500-ml three-necked flask, and 1.3 g (9.9 mmol) of aluminum chloride were added to the mixture in a nitrogen atmosphere at 5° C. Further, a solution of 20.1 g (217 mmol) of t-butylchloride in 30 ml of dichloromethane was dropped to the mixture. After that, the temperature of the mixture was increased to room temperature, and the mixture was stirred for 4 hours. After the reaction, an organic layer was extracted with chloroform, dried with anhydrous sodium sulfate, and purified with a silica gel column (heptane developing solvent), whereby 28.6 g of an adduct (2) (white crystal) were obtained (92% yield).

10 g (31.8 mmol) of the adduct (2) and 200 ml of carbon tetrachloride were loaded into a 500-ml three-necked flask, and 3.6 g (63.6 mmol) of an iron powder were added to the mixture at 5° C. Further, a solution of 51 g (318 mmol) of bromine in 50 ml of carbon tetrachloride was dropped to the mixture. After that, the temperature of the mixture was increased to room temperature, and the mixture was stirred for 8 hours. After the reaction, an organic layer was extracted with chloroform, washed with an aqueous solution of sodium thiosulfate, and dried with anhydrous sodium sulfate. The dried product was purified with a silica gel column (mixed developing solvent of heptane and toluene), whereby 16.6 g of a tetrabromo intermediate (3) (white crystal) were obtained (83% yield).

SYNTHESIS EXAMPLE 1

Synthesis of Exemplified Compound No. 1

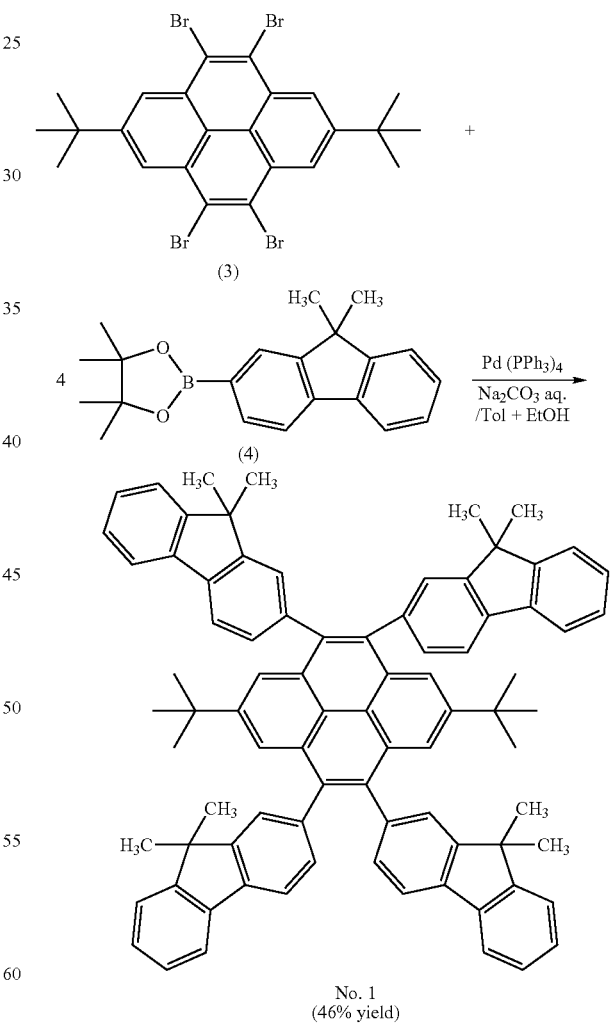

1.0 g (1.59 mmol) of the tetrabromo intermediate (3), 3.0 g (12.7 mmol) of pinacolborane (4), 200 ml of toluene, and 70 ml of ethanol were loaded into a 500-ml three-necked flask. An aqueous solution of 12.8 g of sodium carbonate in 64 ml of water was dropped to the mixture while the mixture was stirred in a nitrogen atmosphere at room temperature. Next, 0.37 g (0.32 mmol) of tetrakis(triphenylphosphine)palladium (0) was added to the mixture. After the mixture had been stirred at room temperature for 30 minutes, the temperature of the mixture was increased to 77° C., and the mixture was stirred for 5 hours. After the reaction, an organic layer was extracted with chloroform, dried with anhydrous sodium sulfate, and purified with a silica gel column (mixed developing solvent of hexane and toluene), whereby 0.79 g of Exemplified Compound No. 1 (white crystal) was obtained (46% yield).

SYNTHESIS EXAMPLE 2

Synthesis of Exemplified Compound No. 7

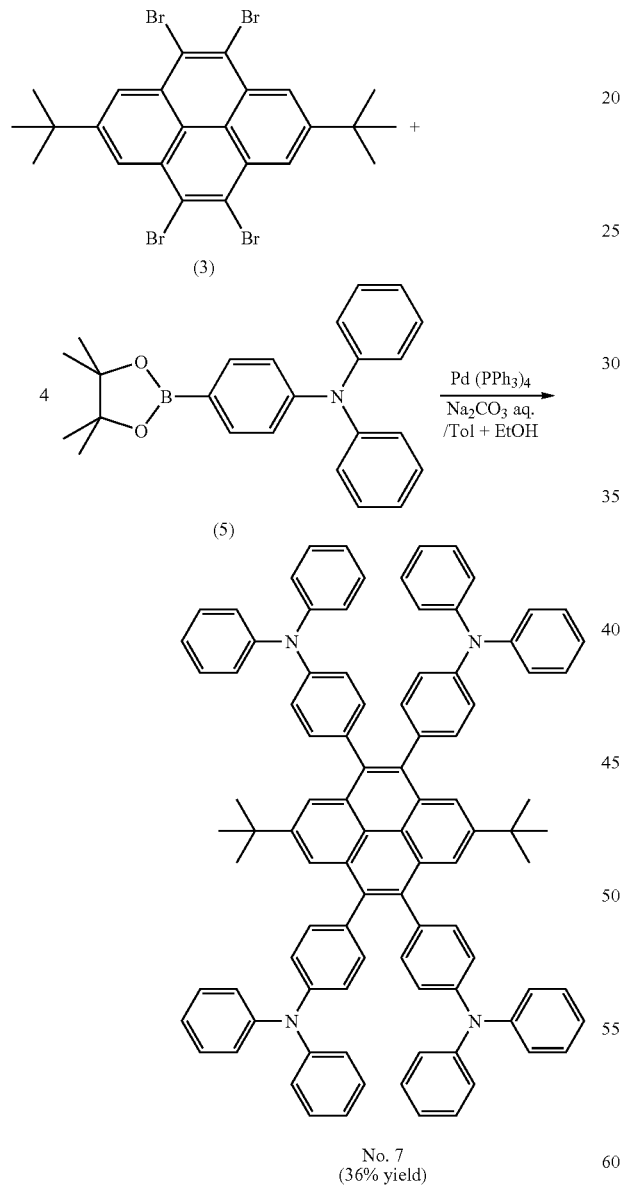

1.0 g (1.59 mmol) of the tetrabromo intermediate (3), 4.7 g (12.7 mmol) of pinacolborane (5), 200 ml of toluene, and 70 ml of ethanol were loaded into a 500-ml three-necked flask. An aqueous solution of 12.8 g of sodium carbonate in 64 ml of water was dropped to the mixture while the mixture was stirred in a nitrogen atmosphere at room temperature. Next, 0.37 g (0.32 mmol) of tetrakis(triphenylphosphine)palladium (0) was added to the mixture. After the mixture had been stirred at room temperature for 30 minutes, the temperature of the mixture was increased to 77° C., and the mixture was stirred for 5 hours. After the reaction, an organic layer was extracted with chloroform, dried with anhydrous sodium sulfate, and purified with a silica gel column (mixed developing solvent of hexane and toluene), whereby 0.74 g of Exemplified Compound No. 7 (white crystal) was obtained (36% yield).

SYNTHESIS EXAMPLE 3

Synthesis of Exemplified Compound No. 17

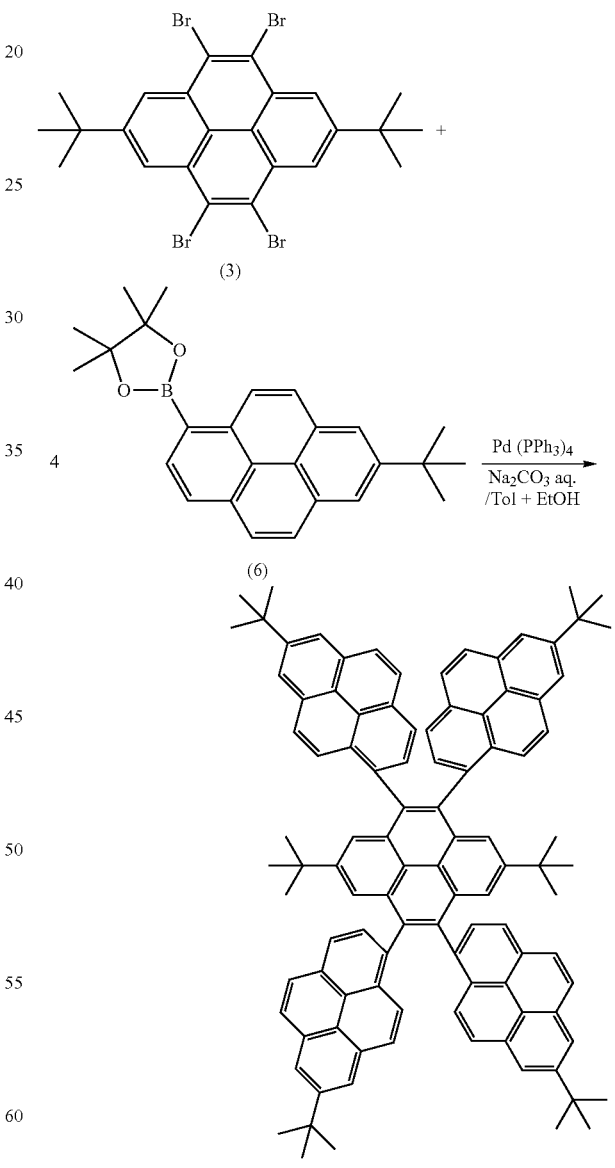

1.0 g (1.59 mmol) of the tetrabromo intermediate (3), 4.9 g (12.7 mmol) of pinacolborane (6), 200 ml of toluene, and 70 ml of ethanol were loaded into a 500-ml three-necked flask. An aqueous solution of 12.8 g of sodium carbonate in 64 ml of water was dropped to the mixture while the mixture was stirred in a nitrogen atmosphere at room temperature. Next, 0.37 g (0.32 mmol) of tetrakis(triphenylphosphine)palladium (0) was added to the mixture. After the mixture had been stirred at room temperature for 30 minutes, the temperature of the mixture was increased to 77° C., and the mixture was stirred for 5 hours. After the reaction, an organic layer was extracted with chloroform, dried with anhydrous sodium sulfate, and purified with a silica gel column (mixed developing solvent of hexane and toluene), whereby 1.2 g of Exemplified Compound No. 17 (white crystal) was obtained (55% yield).

EXAMPLE 1

A device having a structure shown in FIG. 7 was produced.

Indium tin oxide (ITO) as the anode 2 was formed into a film having a thickness of 120 nm by a sputtering method on a glass substrate as the substrate 1, and the resultant was used as a transparent conductive supporting substrate. The resultant substrate was subjected to ultrasonic cleaning in acetone and isopropyl alcohol (IPA) in this order. Then, the substrate was washed in boiling IPA and dried. The substrate was further subjected to UV/ozone cleaning and used as a transparent conductive supporting substrate.

A Baytron P Al-4083 was formed into a film having a thickness of 50 nm by a spin coating method on the transparent conductive supporting substrate, whereby the hole injecting layer 7 was formed.

Further, a 1-wt % solution of Exemplified Compound No. 5 in xylene was formed into a film having a thickness of 50 nm by a spin coating method, whereby the light emitting layer 3 was formed.

Next, calcium was formed into a metal layer film having a thickness of 1 nm by a vacuum deposition method on the above organic layer so as to serve as the electron injecting layer 8. The film was formed at a degree of vacuum at the time of deposition of $1.0 \times 10^{-4}$ Pa and a film formation rate of 0.1 nm/sec.

Further, an aluminum layer having a thickness of 150 nm was formed by a vacuum deposition method so as to serve as the cathode 4. The layer was formed at a degree of vacuum at the time of deposition of $1.0 \times 10^{-4}$ Pa and a film formation rate of 1.0 nm/sec or more to 1.2 nm/sec or less.

Further, the resultant was covered with a protective glass plate in a nitrogen atmosphere and sealed with an acrylic resin-based adhesive.

A DC voltage of 5 V was applied to the thus-obtained device by using the ITO electrode (anode 2) as a positive electrode and the Al electrode (cathode 4) as a negative electrode. As a result, a current flowed in the device at a current density of 40 mA/cm$^2$, and the device was observed to emit blue light having a luminance of 950 cd/m$^2$. The device had chromaticity coordinates NTSC (X, Y) of (0.15, 0.08).

Further, a voltage was applied to the device for 50 hours while a current density was kept at 20.0 mA/cm$^2$. As a result, an initial luminance of 400 cd/m$^2$ reduced to 360 cd/m$^2$ in 50 hours. This result means that luminance degradation was small.

EXAMPLES 2 TO 8

Devices were each produced in the same manner as in Example 1 except that any one of the Exemplified Compounds shown in Table 1 was used instead of Exemplified Compound No. 5, and the devices were each evaluated in the same manner as in Example 1. Table 1 shows the results.

COMPARATIVE EXAMPLES 1 TO 2

Devices were each produced in the same manner as in Example 1 except that any one of the Compounds shown in the following structural formulae was used instead of Exemplified Compound No. 5, and the devices were each evaluated in the same manner as in Example 1. Table 1 shows the results.

TABLE 1

| Example No. | Exemplified Compound No. | Applied voltage (V) | Initial Luminance (cd/m$^2$) | Evaluation for durability (Current density 20 mA/m$^2$) Initial luminance (cd/m$^2$) | Luminance after 50 hours (cd/m$^2$) |
|---|---|---|---|---|---|
| Example 1 | 5 | 5 | 950 | 400 | 360 |
| Example 2 | 11 | 5 | 900 | 360 | 300 |
| Example 3 | 12 | 5 | 1200 | 550 | 520 |
| Example 4 | 13 | 5 | 1050 | 500 | 430 |
| Example 5 | 14 | 5 | 750 | 320 | 290 |
| Example 6 | 15 | 5 | 650 | 300 | 250 |
| Example 7 | 24 | 5 | 800 | 380 | 320 |
| Example 8 | 25 | 5 | 750 | 360 | 300 |
| Comparative Example 1 | Comparative Compound No. 1 | 5 | 600 | 280 | 130 |
| Comparative Example 2 | Comparative Compound No. 2 | 5 | 350 | 150 | 70 |

Comparative Compound No. 1

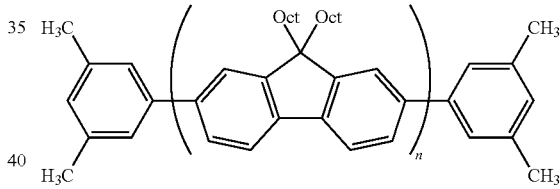

Comparative Compound No. 2

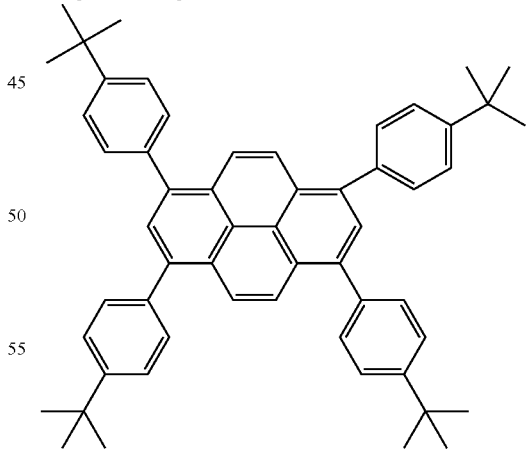

EXAMPLE 9

A device having a structure shown in FIG. 3 was produced.

Indium tin oxide (ITO) as the anode 2 was formed into a film having a thickness of 120 nm by a sputtering method on a glass substrate as the substrate 1, and the resultant was used as a transparent conductive supporting substrate. The resultant substrate was subjected to ultrasonic cleaning in acetone and isopropyl alcohol (IPA) in this order. Then, the substrate was washed in boiling IPA and dried. The substrate was further subjected to UV/ozone cleaning and used as a transparent conductive supporting substrate.

A 2-wt % solution of a diarylamine compound represented by the following structural formula in chloroform was formed into a film having a thickness of 30 nm by a spin coating method on the transparent conductive supporting substrate obtained in the same manner as in Example 1, whereby the hole transporting layer 5 was formed.

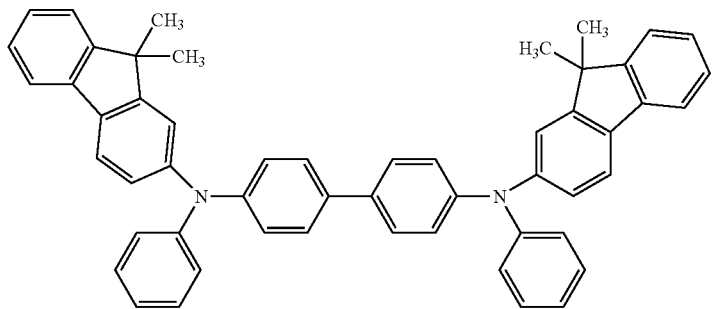

Further, a fluorene compound represented by the following structural formula and Exemplified Compound No. 1 (at a weight ratio of 10:90) were formed into a film having a thickness of 20 nm by a vacuum deposition method, whereby the light emitting layer 3 was formed. The film was formed at a degree of vacuum at the time of deposition of $1.0 \times 10^{-4}$ Pa and a film formation rate of 0.2 nm/sec or more to 0.3 nm/sec or less.

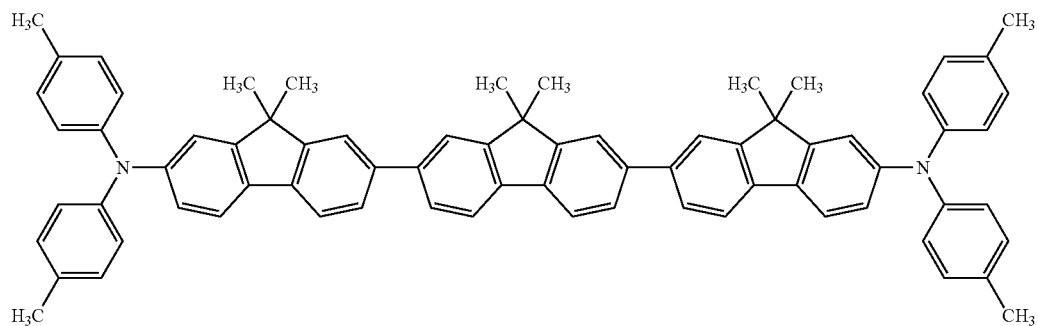

Further, bathophenanthroline was formed into a film having a thickness of 40 nm by a vacuum deposition method, whereby the electron transporting layer 6 was formed. The film was formed at a degree of vacuum at the time of deposition of $1.0 \times 10^{-4}$ Pa and a film formation rate of 0.2 nm/sec or more to 0.3 nm/sec or less.

Next, a deposition material formed of aluminum and lithium (having a lithium concentration of 1 atomic %) was formed into a metal layer film having a thickness of 150 nm by a vacuum deposition method on the above organic layer so as to serve as the cathode 4, whereby the device having a structure shown in FIG. 3 was produced. The film was formed at a degree of vacuum at the time of deposition of $1.0 \times 10^{-4}$ Pa and a film formation rate of 1.0 nm/sec or more to 1.2 nm/sec or less.

Further, the resultant was covered with a protective glass plate in a nitrogen atmosphere and sealed with an acrylic resin-based adhesive.

A DC voltage of 5 V was applied to the thus-obtained device by using the ITO electrode (anode 2) as a positive electrode and the Al electrode (cathode 4) as a negative electrode. As a result, a current flowed in the device at a current density of 60 mA/cm$^2$, and the device was observed to emit blue light having a luminance of 1200 cd/m$^2$.

The device had chromaticity coordinates NTSC (X, Y) of (0.15, 0.08).

Further, a voltage was applied to the device for 100 hours while a current density was kept at 30.0 mA/cm$^2$. As a result, an initial luminance of 550 cd/m$^2$ reduced to 460 cd/m$^2$ in 50 hours. This result means that luminance degradation was small.

EXAMPLES 10 TO 27

Devices were each produced in the same manner as in Example 9 except that any one of the exemplified compounds shown in Table 2 was used instead of Exemplified Compound No. 1, and the devices were each evaluated in the same manner as in Example 1. Table 2 shows the results.

COMPARATIVE EXAMPLE 3

Devices were each produced in the same manner as in Example 9 except that the Comparative Compound No. 2 was used instead of Exemplified Compound No. 1, and the devices were each evaluated in the same manner as in Example 9. Table 2 shows the results.

TABLE 2

| Example No. | Exemplified Compound No. | Applied voltage (V) | Luminance (cd/m²) | Evaluation for durability (Current density 30 mA/cm²) Initial luminance (cd/m²) | Luminance after 100 hours (cd/m²) |
| --- | --- | --- | --- | --- | --- |
| Example 9 | 1 | 5 | 1200 | 550 | 460 |
| Example 10 | 2 | 5 | 1450 | 680 | 600 |
| Example 11 | 3 | 5 | 1200 | 530 | 450 |
| Example 12 | 4 | 5 | 1050 | 450 | 330 |
| Example 13 | 6 | 5 | 950 | 350 | 270 |
| Example 14 | 7 | 5 | 1150 | 550 | 420 |
| Example 15 | 8 | 5 | 1100 | 550 | 440 |
| Example 16 | 9 | 5 | 1050 | 470 | 330 |
| Example 17 | 10 | 5 | 900 | 410 | 310 |
| Example 18 | 16 | 5 | 950 | 400 | 320 |
| Example 19 | 17 | 5 | 1250 | 560 | 430 |
| Example 20 | 18 | 5 | 1050 | 500 | 410 |
| Example 21 | 19 | 5 | 800 | 350 | 290 |
| Example 22 | 20 | 5 | 1000 | 450 | 380 |
| Example 23 | 21 | 5 | 900 | 360 | 270 |
| Example 24 | 22 | 5 | 800 | 330 | 250 |
| Example 25 | 23 | 5 | 750 | 320 | 250 |
| Example 26 | 26 | 5 | 900 | 400 | 300 |
| Example 27 | 27 | 5 | 850 | 330 | 250 |
| Comparative Example 3 | Comparative Compound No. 2 | 5 | 650 | 260 | 120 |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2006-310898, filed Nov. 17, 2006, which is hereby incorporated by reference herein in its entirety.

What is claimed is:

1. A pyrene compound represented by the following general formula (I):

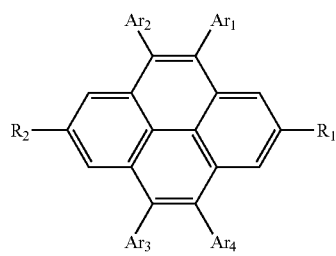

(I)

wherein $R_1$ and $R_2$ each represent a substituted or unsubstituted alkyl group, and $R_1$ and $R_2$ may be identical to or different from each other; and $Ar_1$, $Ar_2$, $Ar_3$, and $Ar_4$ are each represented by the following general formula (II)

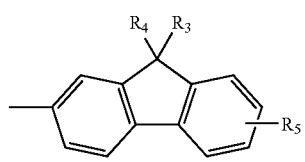

(II)

wherein $R_3$ and $R_4$ each represent a group selected from the group consisting of a substituted or unsubstituted alkyl group, a substituted or unsubstituted aralkyl group, a substituted or unsubstituted aryl group, and a substituted or unsubstituted heterocyclic group, and $R_3$ and $R_4$ may be identical to or different from each other; and $R_5$ represents a group selected from the group consisting of a hydrogen atom, a substituted or unsubstituted alkyl group, a substituted or unsubstituted aralkyl group, a substituted or unsubstituted aryl group, a substituted or unsubstituted heterocyclic group, a substituted or unsubstituted condensed polycyclic aromatic group, a substituted or unsubstituted condensed polycyclic heterocyclic group, a substituted or unsubstituted aryloxy group, a substituted amino group, a halogen atom, and a cyano group.

2. A pyrene compound represented by the following general formula (I):

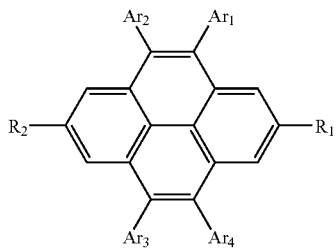

(I)

wherein $R_1$ and $R_2$ each represent a substituted or unsubstituted alkyl group, and $R_1$ and $R_2$ may be identical to or different from each other; and $Ar_1$, $Ar_2$, $Ar_3$, and $Ar_4$ are each represented by the following general formula (III)

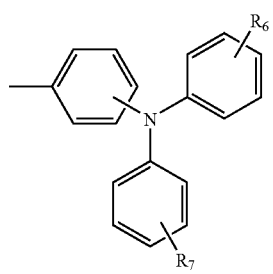

(III)

wherein $R_6$ and $R_7$ each represent a group selected from the group consisting of a hydrogen atom, a substituted or unsubstituted alkyl group, a substituted or unsubstituted aralkyl group, a substituted or unsubstituted aryl group, a substituted or unsubstituted heterocyclic group, a substituted or unsubstituted condensed polycyclic aromatic group, a substituted or unsubstituted condensed polycyclic heterocyclic group, a substituted or unsubstituted aryloxy group, a substituted amino group, a halogen atom, and a cyano group, and $R_6$ and $R_7$ may be identical to or different from each other.

3. A pyrene compound represented by the following general formula (I):

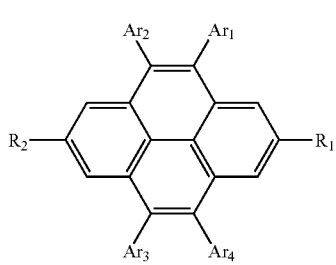

(I)

wherein $R_1$ and $R_2$ each represent a substituted or unsubstituted alkyl group, and $R_1$ and $R_2$ may be identical to or different from each other; and $Ar_1$, $Ar_2$, $Ar_3$, and $Ar_4$ are each represented by the following general formula (IV)

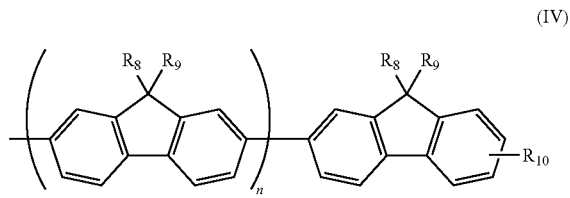

(IV)

wherein $R_8$ and $R_9$ each represent a group selected from the group consisting of an alkyl group, a substituted or unsubstituted aralkyl group, a substituted or unsubstituted aryl group, and a substituted or unsubstituted heterocyclic group, and $R_8$ and $R_9$ may be identical to or different from each other;

$R_{10}$ represents a group selected from the group consisting of a hydrogen atom, a substituted or unsubstituted alkyl group, a substituted or unsubstituted aralkyl group, a substituted or unsubstituted aryl group, a substituted or unsubstituted heterocyclic group, a substituted or unsubstituted condensed polycyclic aromatic group, a substituted or unsubstituted condensed polycyclic heterocyclic group, a substituted or unsubstituted aryloxy group, a substituted amino group, a halogen atom, and a cyano group; and n represents an integer of 1 or more to 9 or less.

4. A pyrene compound represented by the following general formula (I):

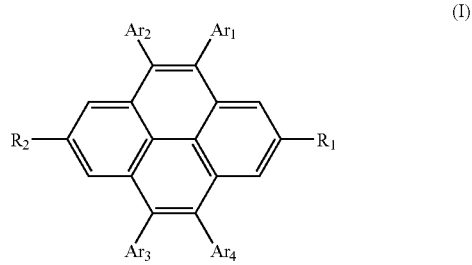

(I)

wherein $R_1$ and $R_2$ each represent a substituted or unsubstituted alkyl group, and $R_1$ and $R_2$ may be identical to or different from each other; and $Ar_1$, $Ar_2$, $Ar_3$, and $Ar_4$ are each represented by the following general formula (V)

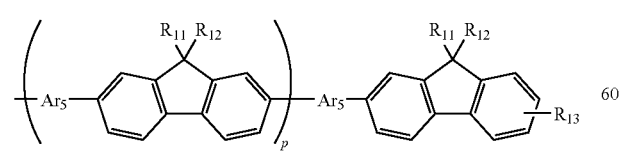

(V)

wherein $R_{11}$ and $R_{12}$ each represent a group selected from the group consisting of an alkyl group, a substituted or unsubstituted aralkyl group, a substituted or unsubstituted aryl group, and a substituted or unsubstituted heterocyclic group, and $R_{11}$ and $R_{12}$ may be identical to or different from each other;

$R_{13}$ represents a group selected from the group consisting of a hydrogen atom, a substituted or unsubstituted alkyl group, a substituted or unsubstituted aralkyl group, a substituted or unsubstituted aryl group, a substituted or unsubstituted heterocyclic group, a substituted or unsubstituted condensed polycyclic aromatic group, a substituted or unsubstituted condensed polycyclic heterocyclic group, a substituted or unsubstituted aryloxy group, a substituted amino group, a halogen atom, and a cyano group;

$Ar_5$ represents a divalent, substituted or unsubstituted aryl group, or a divalent, substituted or unsubstituted condensed polycyclic aromatic group; and p represents an integer of 0 or more to 5 or less.

5. A pyrene compound represented by the following general formula (I):

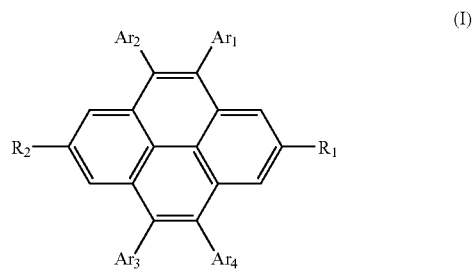

(I)

wherein $R_1$ and $R_2$ each represent a substituted or unsubstituted alkyl group, and $R_1$ and $R_2$ may be identical to or different from each other; and $Ar_1$, $Ar_2$, $Ar_3$, and $Ar_4$ are each represented by the following general formula (VI)

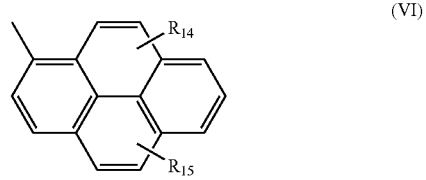

(VI)

wherein $R_{14}$ and $R_{15}$ each represent a group selected from the group consisting of a hydrogen atom, a substituted or unsubstituted alkyl group, a substituted or unsubstituted aralkyl group, a substituted or unsubstituted aryl group, a substituted or unsubstituted heterocyclic group, a substituted or unsubstituted condensed polycyclic aromatic group, a substituted or unsubstituted condensed polycyclic heterocyclic group, a substituted or unsubstituted aryloxy group, a substituted amino group, a halogen atom, and a cyano group, and $R_{14}$ and $R_{15}$ may be identical to or different from each other.

* * * * *